United States Patent [19]

Schmitt et al.

[11] Patent Number: 5,218,206
[45] Date of Patent: Jun. 8, 1993

[54] METHOD FOR DETERMINING THE CONDITION OF A ROADWAY SURFACE

[75] Inventors: Klemens Schmitt, Rothenbach; Walter Schaube, Wipshausen, both of Fed. Rep. of Germany

[73] Assignee: TZN Forschungz- und Entwicklungszentrum Unterlüss GmbH, Unterlüss, Fed. Rep. of Germany

[21] Appl. No.: 776,005

[22] PCT Filed: Nov. 28, 1990

[86] PCT No.: PCT/EP90/02035
§ 371 Date: Nov. 15, 1991
§ 102(e) Date: Nov. 15, 1991

[87] PCT Pub. No.: WO91/14170
PCT Pub. Date: Sep. 19, 1991

[30] Foreign Application Priority Data
Mar. 15, 1990 [DE] Fed. Rep. of Germany ....... 4008280

[51] Int. Cl.⁵ ............. G01N 21/55; G08B 19/02
[52] U.S. Cl. ................. 250/339; 250/340; 250/341; 340/583
[58] Field of Search ........... 250/339, 340, 341, 349; 340/580, 583; 356/445, 447, 448

[56] References Cited

U.S. PATENT DOCUMENTS

| 2,274,091 | 6/1981 | Decker . | |
|---|---|---|---|
| 3,873,927 | 3/1975 | Overall | 340/580 X |
| 4,345,840 | 8/1982 | Goetz et al. | 250/339 X |
| 4,690,553 | 9/1987 | Fukamizu et al. | 356/448 X |
| 4,996,430 | 2/1991 | Gupta | 250/339 |

FOREIGN PATENT DOCUMENTS

| 0005696 | 12/1979 | European Pat. Off. . |
| 2712199 | 9/1978 | Fed. Rep. of Germany . |
| 2912645 | 10/1980 | Fed. Rep. of Germany . |
| 3023444 | 1/1981 | Fed. Rep. of Germany . |
| 3640539 | 6/1988 | Fed. Rep. of Germany . |
| 3816416 | 11/1989 | Fed. Rep. of Germany . |
| 2158939 | 11/1985 | United Kingdom . |

Primary Examiner—Constantine Hannaher
Assistant Examiner—Edward J. Glick
Attorney, Agent, or Firm—Spencer, Frank & Schneider

[57] ABSTRACT

The condition of the roadway with respect to dryness, wetness, or icing is determined, contact-free by way of reflection measurements of light in the infrared range. The reflected light is measured selectively and simultaneously by a receiver in at least two wavelength regions with the wavelength ranges to be determined being in spectral dependence from the surface condition. Formation of a quotient of the detected signals makes possible an unequivocal statement regarding the respective condition of the roadway surface.

14 Claims, 3 Drawing Sheets

METHOD FOR DETERMINING THE CONDITION OF A ROADWAY SURFACE

BACKGROUND OF THE INVENTION

The invention relates to a method and device for the contact-free determination of the condition of a roadway surface, with respect to dryness, wetness or icing, by measuring the reflection of light in the infrared range.

It is known to construct devices which utilize the reflection of radiation to warn of skidding conditions on roads. This can be accomplished, on the one hand, through the emission of radiation in the microwave range by utilizing the different dielectric constants of water and ice (see DE 29 12 645-A1), but also by the reflection of infrared radiation (IR radiation) (see DE 2,712,199-B1, EP 0,005,696-A1 and DE 3,023,444-A1).

DE 2,712,199-B1 and EP 0,005,696-A1 disclose a device for warning of skidding conditions on roadways. In this device, IR radiation, which is produced by two laser diodes, is transmitted by way of IR wave guides into the vicinity of the road surface and from there it is in turn directed to the common receiver by way of IR wave guides.

The wavelength of the measuring light pulses thus lies, at an absorption maximum for ice, in the wavelength regions of 790 to 810 nm, 890 to 920 nm, 1020 to 1060 nm or 1260 to 1290 nm. The second laser diode radiates reference beam pulses whose wavelengths lie in the vicinity of the absorption maximum for ice, but must not be affected by ice nor water nor water vapor.

DE 3,023,444-A1 discloses a device which, by means of a light projector transmits onto the roadway surface IR radiation in a range from 1400 to 2500 nm, in which snow demonstrates less reflectivity than a dry road surface. Three modified arrangements are recommended for determining roadway conditions:

One configuration is based on an IR radiation source in a range from 1400 to 2500 nm and employs two sensors in the IR range of which the first detects mirror reflected light and the second reflected scattered light on the surface. Additionally, the temperature is measured with a thermometer.

The second configuration dispenses with the thermometer and the light within the range of the visible spectrum and in the IR range between 1400 and 2500 nm is beamed onto the surface. Two sensors serve to measure the reflected radiation in the visible and in the IR range.

The third configuration also makes its determination by means of a light source which emits IR radiation in a range from 1400 to 2500 nm and visible light in a range from 500 to 1090 nm. is equipped with a detector for scattered IR light, a detector for scattered light in the visible range, a detector for mirror reflected light in the visible range and a temperature measuring device.

In all three configurations, the signals measured with the individual sensors are compared by way of logic circuits in an evaluation unit having stored patterns of reference signals in order to specify the road conditions.

Determination of the surface condition (dry, wet, icy) of a roadway is of extreme significance for traffic safety.

Sensor systems already exist which require the sensor to contact the surface to be examined, and others that operate without contact, which are based on reflection measurements. The existing solutions are structurally elaborate and expensive and the detection reliability of these systems is limited.

The devices disclosed in DE 3,023,444-A1 which also use broad-band IR radiation for irradiation are very expensive with respect to the devices required for signal pattern comparison. In particular, a comparison using previously stored signal patterns is made.

The first embodiment listed there, in which IR radiation in the wavelength region from 1400 to 2500 nm is used, permits a differentiation between a wet or icy road condition only by way of an additional temperature measurement. The other embodiments, in addition to radiation of light in the IR range from 1400 to 2500 nm, also contain light components in the visible range from 500 to 1090 nm, which are detected by separate detectors as scattered and mirror reflected light. Under certain conditions, this could result in transverse sensitivities due to the incidence of sunlight.

The device according to DE 2,712,199-B1 and EP 0,005,696-A1 employs two pulse light sources (laser diodes), but only one detector, so that the measurement can only be performed sequentially.

Since the selection of wavelengths is already made before the surface is struck, and the radiation is not filtered at the input of the detector, interference may also occur here due to the radiation from further light sources. This is to be prevented by the radiation of reference radiation pulses. However, the wavelength of these pulses is selected such that the reflection is specifically influenced neither by ice nor water. Accordingly, this would involve a wavelength at which ice and water exhibit the same reflectivity, which is, in addition, as independent as possible of different layer thicknesses. The wavelength of the measuring light pulse lies within an absorption maxima for ice. However, there is only a minor difference between the absorption maxima for ice and water in the preferably used wavelength range, so that an adequate wavelength stability of the measuring light pulses must be ensured. This is critical in laser diodes, because they exhibit a not insignificant wavelength drift, depending on the temperature. If laser diodes are used, costly temperature stabilization is therefore necessary.

In the devices according to EP 0,005,691-A1 and DE 2,712,199-B1 filters are additionally used in the radiation path. However, with strong drifts the result of this is that only minimal or no light intensity remains available for reflection on the surface. Furthermore, if the drift of the two diodes is not uniform, falsification of the resulting signal levels might occur.

SUMMARY OF THE INVENTION

It is the object of the present invention to develop a structurally simple and cost-efficient device which differentiates contact-free and with great reliability between the three surface conditions: wet, dry and icy.

The object of the present invention is attained by way of reflection measurements of light in the infrared range. The reflected light is measured selectively and simultaneously by a receiver in at least two wavelength ranges, with the wavelength ranges being spectrally dependent on the surface condition and being selected so that formation of a quotient of the detected signals makes possible an unequivocal statement regarding the respective condition of the roadway surface.

The two wavelength ranges are selected so that the quotient or ratio of the respective detected signals for a wet surface is independent of layer thickness and so that the ratio or quotient of the respective detected signals for any icy surface is at least twice the ratio for a wet surface.

BRIEF DESCRIPTION OF THE DRAWINGS

The invention is described below with the help of embodiments and by way of the figures wherein:

FIG. 1, 1a and

DETAILED DESCRIPTION OF THE PREFERRED EMBODIMENTS

Figure 1:
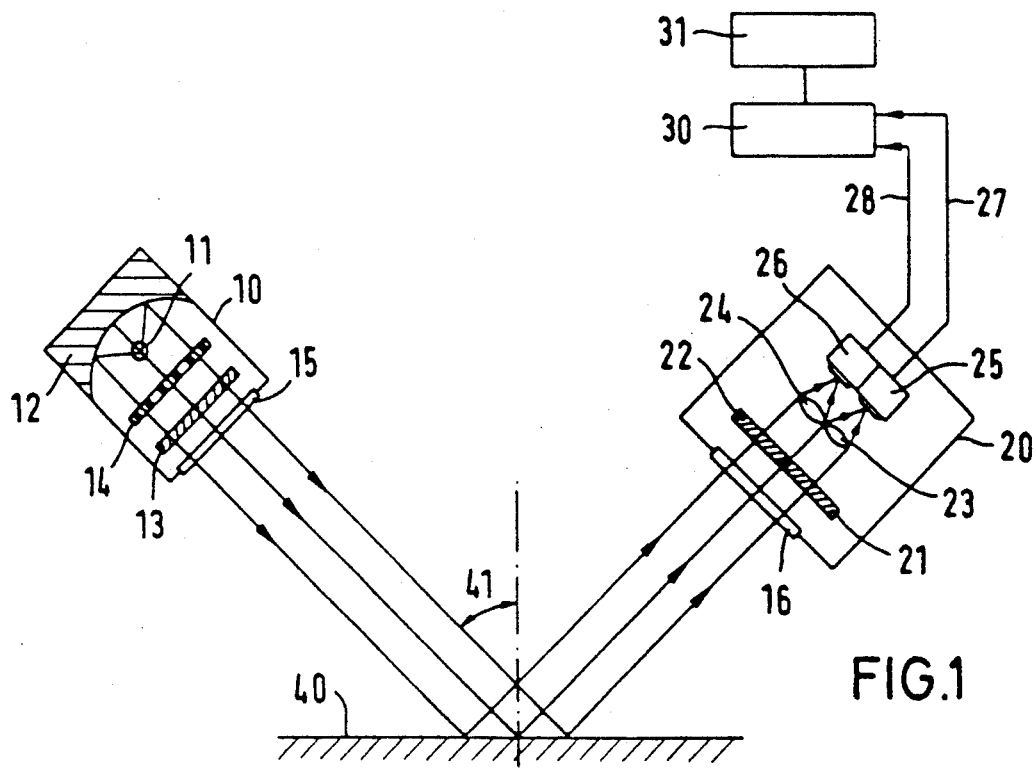

In FIG. 1, reference numeral 10 is a light source housing in which is disposed an IR radiation source 11 (for example, a halogen lamp), a curved reflector mirror 12 and a modulator 14. An optical filter 13 (for example, a long-pass edge filter or an interference filter) can be attached to the output of the source. In order to keep foreign substances from the optical components, the light source housing 10 is closed with a window 15 that permits IR radiation to penetrate.

The system's receiver 20 comprises two interference filters 21, 22, two lenses 23, 24 and two detectors 25, 26.

Receiver 20 is also provided with a window 16 in order to protect the components from, for example, soiling by splashing water.

The outlets of detectors 25, 26 are connected to a signal processor 30 by way of two signal conductors 27, 28. The processor in turn is connected to a signal output interface 31.

Figure 1A:
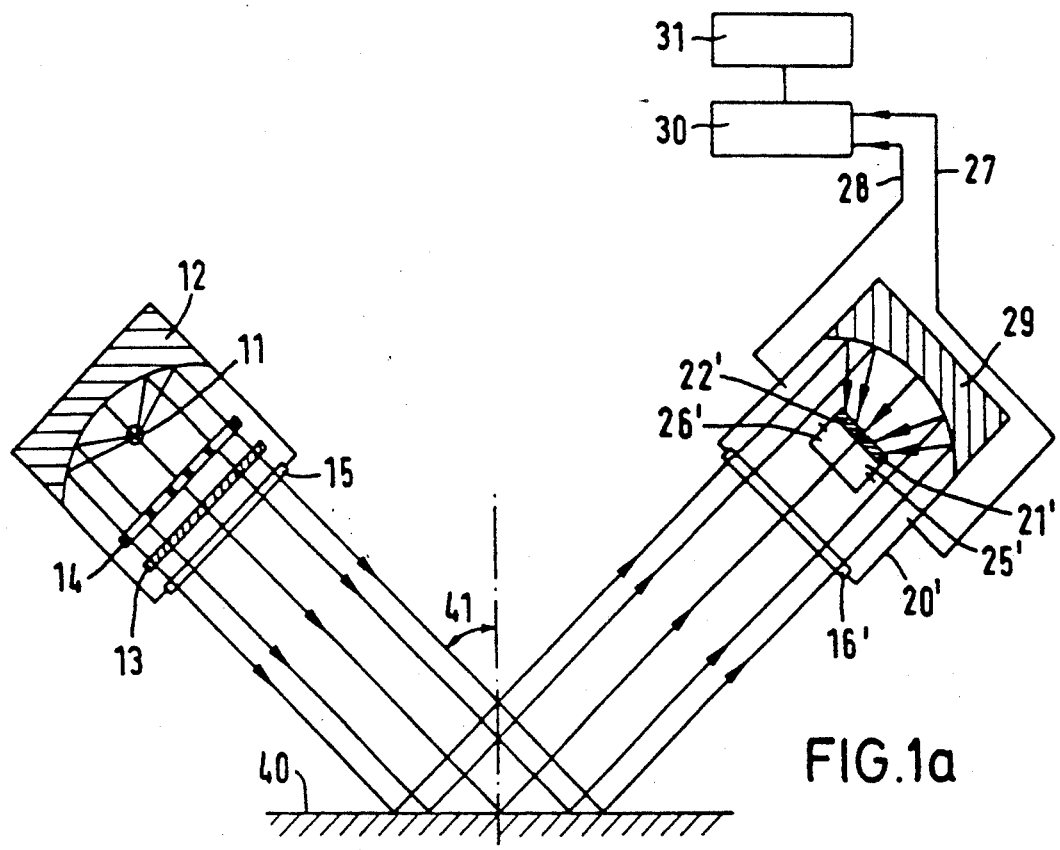

FIG. 1a shows a further device for the detection of IR radiation reflected on the roadway surface 40. The shown light source housing 10, including the respective components, corresponds to that in FIG. 1. Receiver 20' is modified in such way that in this arrangement lenses 23, 24 are dispensed with. Subsequent to entry through window 16', the reflected IR radiation strikes a focussing mirror or reflector 29, in whose focal point two detectors 25', 26', including interference filters 21', 22', which are connected ahead of them, are disposed.

Figure 1B:
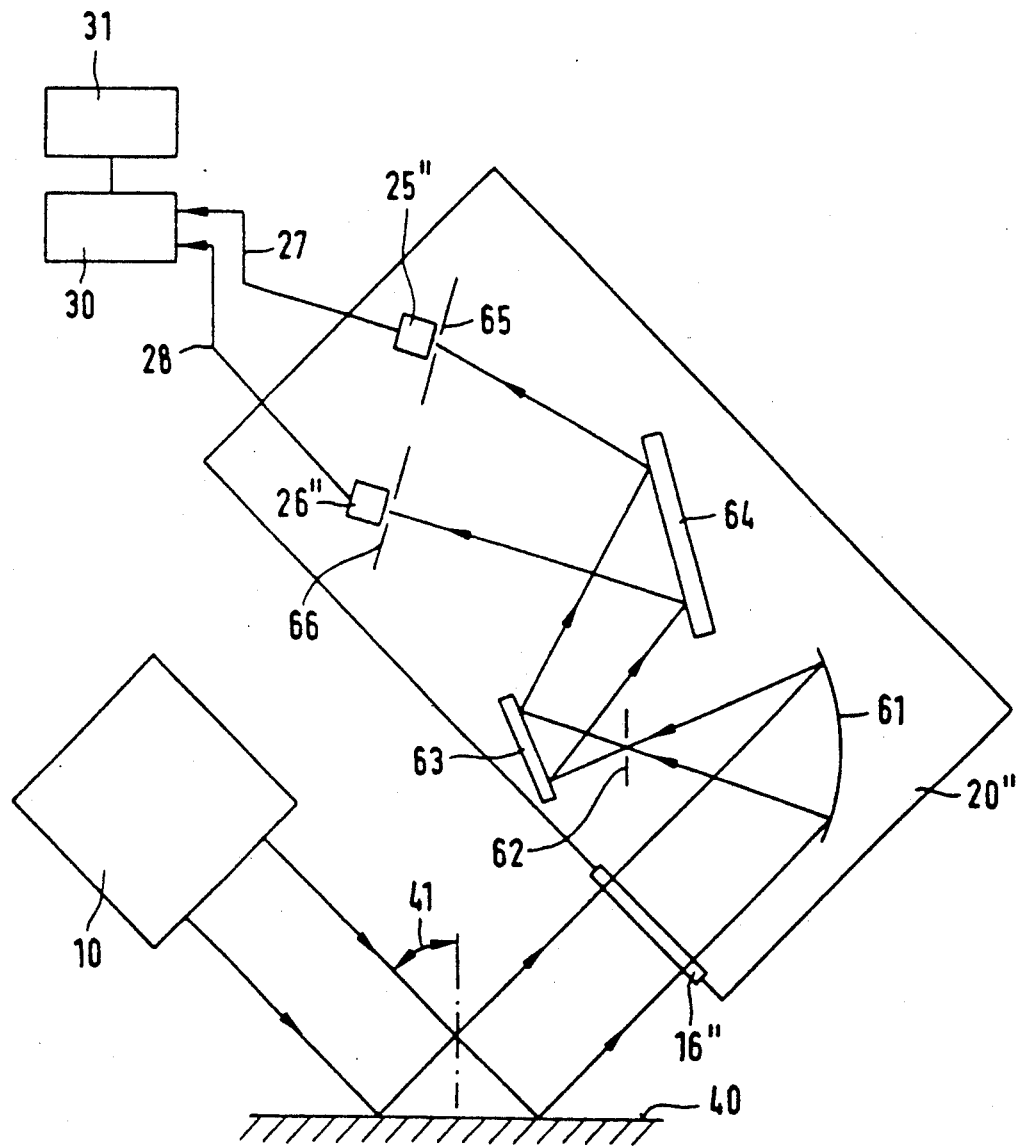
FIG. 1b are schematic illustrations of devices according to the invention for the detection of reflected radiation in the IR range, comprising a light source, receiver and signal processing unit.

FIG. 1b shows a further embodiment for the wavelength selective detection of IR radiation reflected from roadway surface 40. The light source housing 10 including the components which are not shown here, corresponds again to the arrangements according to FIGS. 1 and 1a. The receiver 20" is provided with a window 16" and a parabolic mirror 61 in whose focal point an aperture 62 is arranged. The radiation is separated spectrally by means of a reflecting grating 63 and focussed by way of a focussing mirror 64 onto apertures 65, 66 behind which sensors 25", 26" are disposed.

For further signal processing such as in the arrangements of FIGS. 1 and 1a, the signal processor 30 and the signal output interface 31 are provided. Light source housing 10 and receiver 20, 20', 40" are arranged at an angle $\alpha$ 41 relative to the normal of the roadway surface 40 to be examined. The selection of small angles ($\alpha < 30°$) is advisable. Larger angles are possible if the value of the reflection coefficient, which changes with angle $\alpha$, is taken into consideration, respectively.

Figure 2:
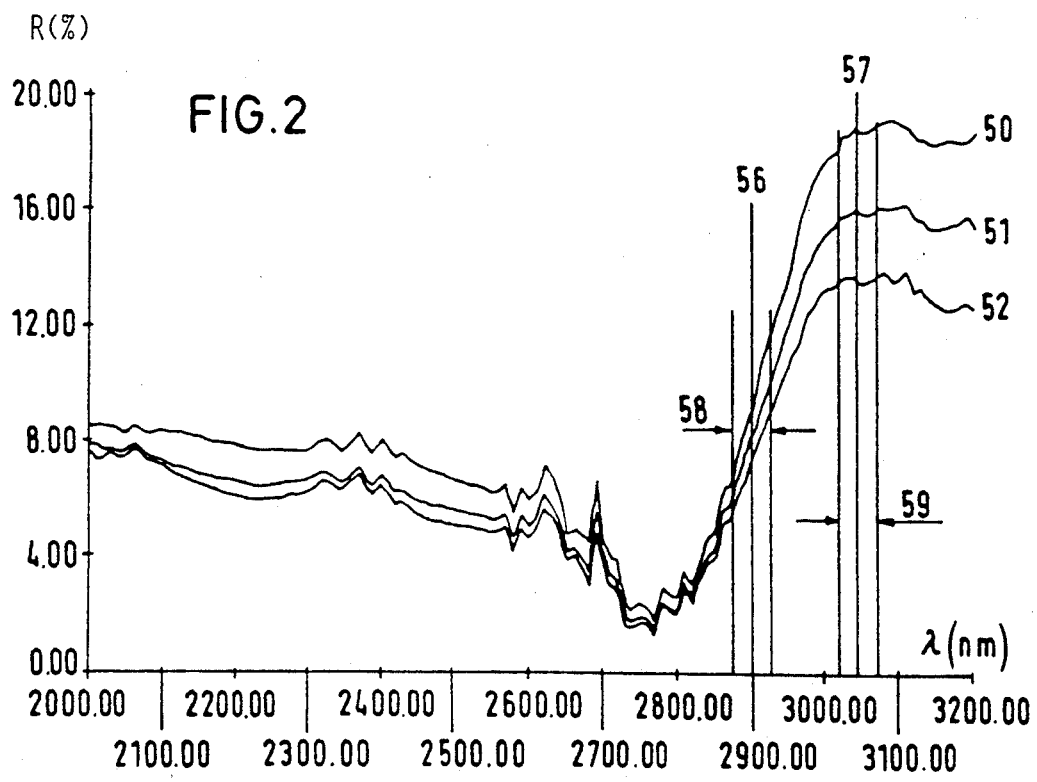
FIG. 2 illustrates the reflectivity of water in dependence on the wavelength in the range from 2000 to 3200 nm at layer thicknesses of 1.0 mm, 1.5 mm and 2.0 mm.

In FIG. 2 the reflectivity R of water, in percent, is plotted over the wavelength in nm. Reference numeral 50 identifies the reflectivity of water having a layer thickness of 2.0 mm; reference numerals 51 and 52 correspond to the reflectivity at layer thicknesses of 1.5 and 1.0 mm. Reference numeral 56 identifies the central wavelength of interference filters 22, 22' at 2900 nm. The spectral width 58 of interference filter 22, 22' is 50 nm. Reference numeral 57 identifies the central wavelength of interference filter 21, 21' at 3050 nm, with the spectral width 59 of interference filter 21, 21' also being 50 nm.

Figure 3:
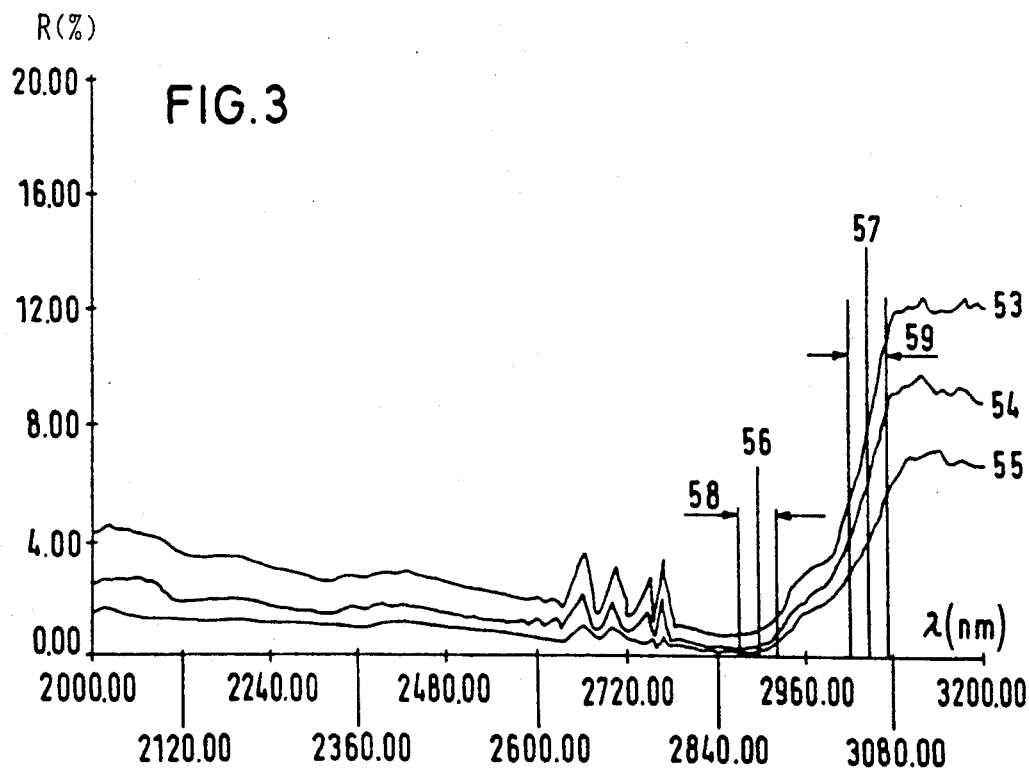
FIG. 3 illustrates the reflectivity of ice in dependence on the wavelength in the range of 2000 to 3200 nm at layer thickness of 1.0 mm, 1.5 mm and 2.0 mm.

FIG. 3 shows the reflectivity R, in percent, of ice in dependence on the wavelength. Reference numerals 53, 54, 55 identify layer thicknesses of 2.0 mm, 1.5 mm and 1.0 mm. The central wavelengths and spectral widths in this figure correspond to those in FIG. 2.

The broadband radiation emitted from light source 11 is focussed by way of a curved reflector mirror 12 and is directed onto the surface to be examined (for example roadway surface 40).

Due to an optic filter 13 attached at the output of source 11 (for example, a longpass edge filter or interference filter) the radiation spectrum can already be preselected. This prevents unacceptably intensive heating of the illuminated roadway surface 40 due to radiation from source 11. The spectral pre-selection can also be accomplished by way of a reflective coating (for example, IR reflective). The radiation is time-modulated by means of a modulator or chopper 14.

Radiation reflected by the roadway surface 40 is spectrally limited in the receiver 20 by means of two interference filters 21, 22 and is focussed onto detectors 25, 26 by way of two lenses 23, 34. As an alternative, filtering of the radiation may also take place between lenses 23, 24 and detectors 25, 26. This has the advantage, as in the arrangement according to FIG. 1a, in which IR radiation is focussed, by way of a curved mirror 29, onto two detectors 25', 26' equipped with interference filters 21', 22' which are connected ahead of them, that smaller interference filters 21', 22' may be used and, as a consequence, costs can be reduced. This makes possible the optional arrangement of using, in place of one focussing reflector 29, two separate focussing reflectors 29 (not shown), which have a smaller diameter and in whose focal points the respective interference filter/detector combinations 21'/25' and 22'/26' are disposed. Attachment of these components can be performed by means of a holding clamp (not shown) which is fastened to the interior of receiver housing 20'.

Interference filters 21, 22; 21', 22' are transparent for two different wavelengths $\lambda$ i and $\lambda$ j at a bandwidth of the transmission range of $\Delta\lambda_i$ and $\Delta\lambda_j$, respectively.

In the arrangement according to FIG. 1b, no interference filters 21, 22; 21', 22' are used for wavelength selection. Instead, the light reflected by roadway 40 is beamed by parabolic mirror 61 through an aperture 62 arranged at the focal point onto a reflection grating 63. The light reflected from grating 63 is selected according to wavelength, depending on the angle, and is focussed by way of mirror 64 to apertures 65, 66, behind which detectors 25"; 26" are arranged.

In this embodiment, the detection of wavelengths $\lambda_i$ and $\lambda_j$ occurs by way of the local arrangement of apertures 65, 66 and detectors 25", 26". These are arranged relative to grating 63 in such a way that only light in wavelength range $\Delta\lambda_i$ for central wavelength $\lambda_i$ strikes detector 25" through aperture 65, and in range $\Delta\lambda_j$ through aperture 66 strikes detector 26".

In comparison to the receivers 20, 20' shown in FIGS. 1 and 1a, the arrangement according to FIG. 1b has the advantage that interference filters 21, 22; 21', 22' can be dispensed with. The maximal transmission for interference filters is usually merely 50%. The use of a reflection grating 63 and mirror 64, by contrast, permits doubling of the light yield, since its reflection losses are very minor, so that, in an advantageous manner, the power of IR radiation source 11 can be reduced by half, resulting in lower operating costs.

Detectors 25, 26; 25', 26'; 25", 26" are designed in such a way that the output voltages $U_i$ and $U_j$ are proportional to the radiation power which is received at wavelengths $\lambda_i$ and $\lambda_j$. Signals voltages $U_i$ and $U_j$ can be individually amplified in accordance with sensitivity characteristics of detectors 25, 26; 25', 26'; 25", 26" and of the spectral emission characteristic of IR source 11, and can subsequently be supplied to signal processor 30.

According to the invention, the ratio of signal voltages $U_i$ and $U_j$ is formed in signal processor 30. The value of quotient $U_i/U_j$ depends on the condition of the irradiated surface. The voltage quotient determined in signal processor 30 is associated with one of the three conditions: dry, wet, icy. Subsequently, a signal corresponding to the condition can then be generated and transmitted to signal output interface 31. With this output signal it is possible, for example, to produce an acoustic or optical signal which corresponds unequivocally to the surface conditions: wet, dry or icy.

The example given here is based on the following spectral values:

$\lambda_i = 3050$ nm, $\lambda_j = 2900$ nm, $\Delta\lambda_i = \Delta\lambda_j = 50$ nm.

$\lambda_i$ and $\lambda_j$ lie each in the center of the 50 nm-wide transmission range.

Calibration of the system, which yields a $U_i/U_j$ value of approximately 1 for a dry surface, yields $U_i/U_j$ values of approximately 2.0 for wet surfaces of different water-film thicknesses, and yields $U_i/U_j$ values which exceed 5 (between 5 and 20) for iced surfaces of different layer thicknesses of ice.

These numerical values were taken from the reflection spectra shown in FIG. 2 and FIG. 3, which show samples of the measured reflection from wet and icy roads having different water and ice layer thicknesses. Angle $\alpha$ 41 was approximately 15° in the measurements; a halogen lamp was used as light source.

FIG. 2 and FIG. 3 show that the increase in the reflection curves in the range from 2700 nm to 3200 nm differ for water and ice. The rising slope of the curve for ice is shifted by approximately 100 nm into the long wave. Measurements show that further equivalent changes of the reflection factor do not occur within the wavelength range from 400 nm to 3500 nm. In addition to the numerical values given here further suitable $\lambda_i$ and $\lambda_j$ values with corresponding $\Delta\lambda_i$ and $\Delta\lambda_j$ values can be selected with the help of FIG. 2 and FIG. 3, and which also result in a $U_i/U_j$ signal value which makes possible an unequivocal association to the surface conditions: dry, wet or icy.

Forming a quotient of signal voltages $U_i$ and $U_j$ has the advantage that the system also operates reliably if the absolute values of $U_i$ and $U_j$ vary over a wide range such as is the case, for example, with different layer thickness of ice (see FIG. 3). It follows from FIG. 2 and FIG. 3 that for the wavelength range of $\lambda > 2700$ nm, reflection values $\lambda_i$ and $\lambda_j$ increase or decrease approximately by the same factor at different ice and water layers, respectively.

A variation in the power of light source 11, which indirectly illuminates both detectors 25, 26; 25', 26'; 25", 26" simultaneously, as well as the different arrangements of radiation source 11 and receiver 20, 20', 20", are also largely compensated by the formation of quotient $U_i/U_j$.

The narrow-band filtration of radiation initially occurs at the input of detectors 25, 26; 25', 26'; 25", 26". This has the advantage that light from additional radiation sources (for example, radiation from the sun) falling on the detectors is also limited to transmission wavelengths $\lambda_i$ and $\lambda_j$ of interference filters 21, 22; 21', 22' and to the selected wavelength radiation which is dependent on the angle. Disruption of the measuring system on account of this radiation can be considered to be low for measuring wavelengths exceeding 2700 nm.

The system for two measured wavelengths $\lambda_i$ and $\lambda_j$ described here, can be expanded analogously to three or more measuring wavelengths.

Thus, the advantages over prior art are that disturbances due to foreign light are negligible. Since the measuring wavelengths lies in a wavelength range in which the reflective behavior demonstrates a spectral dependence from the surface condition, i.e., in the wavelength range from 2700 to 3200 nm, it is possible with the help of the quotient formed by signal voltages $U_i$ and $U_j$ to characterize the surface condition with great reliability. The reliability in this case is not affected by different thicknesses of water and ice layers.

Possible ice formation is not stopped by the intensity of radiated light which is too strong, since the radiation is already weakened due to pre-selection through optical filter 13. Furthermore, the possibility exists of directing the light only in intervals onto the roadway surface 40 to be examined (for example, by means of a movable aperture).

What is claimed is:

1. Method for contact-free determination of a roadway surface condition with respect to dryness, wetness or icing, by means of measuring the reflection of light in the infrared range, comprising the steps of:

illuminating the surface to be examined by a broadband light source;

simultaneously measuring the reflected light in two selected wavelength ranges, with the reflected light in said selected wavelength ranges being spectrally dependent on the surface condition and providing respective signal voltages corresponding to the power received in the two wavelength ranges;

forming a ratio of said signal voltages corresponding to the power received in the individual wavelength ranges; and wherein the two wavelength ranges are selected such that the ratio of said signal voltages for a dry surface is within a first value range, the ratio of said signal voltages for a wet surface is independent of layer thickness and lies within a second value range which is greater than said first value range, and the ratio of said signal voltages for an icy surface is at least twice said ratio of said signal voltages for a wet surface.

2. Method according to claim 1, wherein the selected wavelength ranges are narrow-band wavelength ranges which lie in a spectral range of 2700 nm to 3200 nm.

3. Method according to claim 2, wherein said selected narrow-band wavelength ranges are approximately 50 nm in bandwidth and are centered at 2900 nm and 3050 nm.

4. Method according to claim 1 wherein: said broadband light source is provided with a modulator which is connected ahead of said light source; and a receiver for the reflected light includes a plurality of sensors and a plurality of interference filters, each of which exhibits its maximal transmission in a different one of said wavelength ranges.

5. Method according to claim 4, wherein a signal processor is connected to the output of the receiver to form the ratio of the signal voltages.

6. Method according to claim 1 wherein the reflected light is detected in a receiver by way of a reflection grating in dependence on the angles of the radiation from the grating corresponding to the selected wavelengths.

7. Method according to claim 4, wherein the light reflected from the roadway surface is reflected onto the reflection grating by a parabolic mirror through an aperture disposed in the focal point of said mirror, and the radiation from the grating, in dependence on the angle which is selected according to the desired wavelength, is focussed by a further mirror onto respective sensors through respective apertures.

8. Method according to claim 6, wherein a signal processor is connected to the output of the receiver to form the ratio of the signal voltages.

9. Apparatus for contact-free determination of roadway condition surface with respect to dryness, wetness or icing by measuring the reflection of light in the infrared range comprising broadband light source for illuminating the surface to be examined;

receiver means for receiving and for simultaneously measuring light reflected from the roadway surface in two selected wavelength ranges in which said reflected light is spectrally dependent on the surface condition to provide respective output signal voltages corresponding to the received power in the respective wavelength ranges, with said two wavelength ranges being selected such that the ratio of said output signal voltages for a dry surface is within a first value range, the ratio of said signal voltages for a wet surface is independent of layer thickness and lies within a second value range which is greater than said first value range, and the ratio of said signal voltages for an icy surface is at least twice said ratio of said signal voltages for a wet surface; and means for forming the ratio of the signal voltages corresponding to the power received in the individual spectral ranges and for providing a corresponding output signal value as an indication of the surface condition.

10. Apparatus according to claim 9, wherein said wavelength ranges are narrow-band wavelength ranges which lie in a spectral range of approximately 2700 nm to 3200 nm.

11. Apparatus according to claim 10, wherein said receiver means includes a reflecting grating unto which the reflected light from the roadway surface is directed and detectors for detecting the radiation from the grating in dependence on the angle of the radiation from the grating corresponding to the selected wavelengths.

12. Apparatus according to claim 11, wherein said receiver means further includes, a parabolic mirror positioned to reflect the light reflected from the roadway onto the reflection grating through an aperture disposed in the focal point of said mirror, and a further mirror positioned to direct the radiation from the grating onto said detectors through respective apertures positioned at angles relative to the grating corresponding to said selected wavelengths.

13. Apparatus according to claim 9, wherein a light modulator is provided between said broad-band light source and the roadway surface to be examined, and said receiver means includes a plurality of sensors and associated interference filters with each filter exhibiting its maximal transmission in a different one of said wavelength ranges 14. Apparatus according to claim 9, wherein said means for forming a ratio comprises a signal processor connected to the output of said receiver means and forming a quotient of said signal voltages.

* * * * *

UNITED STATES PATENT AND TRADEMARK OFFICE
CERTIFICATE OF CORRECTION

PATENT NO. : 5,218,206
DATED : June 8th, 1993
INVENTOR(S) : Klemens SCHMITT et al.

It is certified that error appears in the above-indentified patent and that said Letters Patent is hereby corrected as shown below:

On the Title Page, Item [73]:
    change "Forschungz-" to --Forschungs- --.

Signed and Sealed this

Nineteenth Day of April, 1994

*Attest:*

BRUCE LEHMAN

*Attesting Officer*     *Commissioner of Patents and Trademarks*